(12) United States Patent
Ricciardelli

(10) Patent No.: US 8,460,203 B2
(45) Date of Patent: Jun. 11, 2013

(54) GAS FLOW DIVERTER FOR RESPIRATORY MONITORING DEVICE

(75) Inventor: Robert H. Ricciardelli, Waukesha, WI (US)

(73) Assignee: Treymed, Inc., Sussex, WI (US)

( * ) Notice: Subject to any disclaimer, the term of this patent is extended or adjusted under 35 U.S.C. 154(b) by 69 days.

(21) Appl. No.: 12/973,024

(22) Filed: Dec. 20, 2010

(65) Prior Publication Data

US 2011/0083669 A1    Apr. 14, 2011

Related U.S. Application Data

(62) Division of application No. 10/863,697, filed on Jun. 8, 2004, now Pat. No. 7,878,980.

(60) Provisional application No. 60/478,706, filed on Jun. 13, 2003.

(51) Int. Cl.
*A61B 5/08*    (2006.01)

(52) U.S. Cl.
USPC .......................................... 600/538; 600/529

(58) Field of Classification Search
USPC ................................................. 600/529–543
See application file for complete search history.

(56) References Cited

U.S. PATENT DOCUMENTS

| | | | |
|---|---|---|---|
| 4,083,245 A | 4/1978 | Osborn | 73/207 |
| 4,274,425 A | 6/1981 | Lutz et al. | 128/719 |
| 4,382,806 A | 5/1983 | Hakala et al. | 55/18 |
| 4,413,632 A | 11/1983 | Schlessinger et al. | 128/716 |
| 4,539,984 A | 9/1985 | Kiszel et al. | 128/204.23 |
| 4,592,368 A | 6/1986 | Ricciardelli et al. | 128/719 |
| 4,713,095 A | 12/1987 | Ricciardelli | 55/189 |
| 4,852,583 A | 8/1989 | Walker | 128/716 |
| 4,989,456 A | 2/1991 | Stupecky | 73/861.53 |
| 4,993,269 A | 2/1991 | Guillaume et al. | 73/861.53 |
| 4,995,400 A | 2/1991 | Boehringer et al. | 128/725 |
| 5,033,312 A | 7/1991 | Stupecky | 73/861.53 |
| 5,038,621 A | 8/1991 | Stupecky | 73/861.65 |
| 5,044,199 A * | 9/1991 | Drexel et al. | 73/202 |
| 5,067,492 A | 11/1991 | Yelderman et al. | 128/719 |
| 5,088,332 A | 2/1992 | Meriläinen et al. | 73/861.65 |
| 5,101,817 A | 4/1992 | Etter | 128/200.26 |
| 5,178,155 A | 1/1993 | Mault | 128/718 |
| 5,197,895 A | 3/1993 | Stupecky | 439/194 |
| 5,201,322 A | 4/1993 | Henry et al. | 128/719 |
| 5,213,109 A | 5/1993 | Susi | 128/719 |
| D342,135 S | 12/1993 | Goldberger et al. | D24/129 |
| 5,287,851 A | 2/1994 | Beran et al. | 128/204.23 |
| 5,313,955 A | 5/1994 | Rodder | 128/725 |
| D348,616 S | 7/1994 | Apigian et al. | D10/96 |

(Continued)

*Primary Examiner* — Michael Kahelin
*Assistant Examiner* — Karen Toth
(74) *Attorney, Agent, or Firm* — Boyle Fredrickson, S.C.

(57) ABSTRACT

A gas flow diverter for increasing the turbulence of an incoming respiratory gas flow through a respiratory gas sensor is provided. The diverter is positioned at a patient or inlet end of a tube section of the sensor in order to divert the respiratory gas flow from the patient generally equally across the cross-sectional area of the tube section. The diverter can be formed integrally as a part of the sensor, or can be releasably attached to the sensor or to an adapter that is releasably connected to the inlet end of the sensor for use in situations in which the volume of the incoming respiratory gas flow from the patient is greatly reduced due to the size of the patient, i.e., when the patient is an infant.

11 Claims, 5 Drawing Sheets

U.S. PATENT DOCUMENTS

| | | |
|---|---|---|
| 5,347,843 A | 9/1994 | Orr et al. .............................. 73/3 |
| 5,357,972 A | 10/1994 | Norlien ......................... 128/725 |
| 5,379,650 A | 1/1995 | Kofoed et al. ............. 73/861.52 |
| 5,398,695 A | 3/1995 | Anderson et al. ............. 128/719 |
| 5,443,075 A | 8/1995 | Holscher ...................... 128/725 |
| 5,503,151 A | 4/1996 | Harnoncourt et al. ... 128/660.02 |
| 5,535,633 A | 7/1996 | Kofoed et al. ............. 73/861.52 |
| 5,564,432 A | 10/1996 | Thomson ...................... 128/725 |
| 5,565,630 A | 10/1996 | Shene ....................... 73/861.53 |
| 5,598,839 A | 2/1997 | Niles et al. ............... 128/205.23 |
| 5,616,158 A | 4/1997 | Biendarra et al. ............. 55/275 |
| 5,620,004 A | 4/1997 | Johansen ..................... 128/716 |
| 5,676,131 A | 10/1997 | Anderson et al. ........ 128/204.22 |
| 5,722,392 A | 3/1998 | Skimming et al. ....... 128/203.12 |
| 5,789,660 A | 8/1998 | Kofoed et al. .................. 73/23.2 |
| 5,861,546 A * | 1/1999 | Sagi et al. .................. 73/40.5 R |
| D413,825 S | 9/1999 | Storsved ........................ D10/96 |
| 6,142,148 A | 11/2000 | Weckstrom et al. ..... 128/204.22 |
| 6,164,141 A | 12/2000 | Chalvignac et al. ........ 78/861.52 |
| 6,164,142 A | 12/2000 | Dimeff ........................ 73/861.61 |
| 6,216,692 B1 | 4/2001 | Todokoro et al. ........ 128/205.23 |
| 6,324,917 B1 | 12/2001 | Mack et al. ................. 73/861.52 |
| 6,358,215 B1 * | 3/2002 | Ricciardelli .................. 600/532 |
| 6,488,635 B1 * | 12/2002 | Mottram ...................... 600/551 |
| 6,512,581 B1 | 1/2003 | Yamamori et al. ........... 356/246 |
| 6,516,801 B2 | 2/2003 | Boussignac ............. 128/204.24 |
| 6,659,962 B2 | 12/2003 | Ricciardelli .................. 600/538 |

* cited by examiner

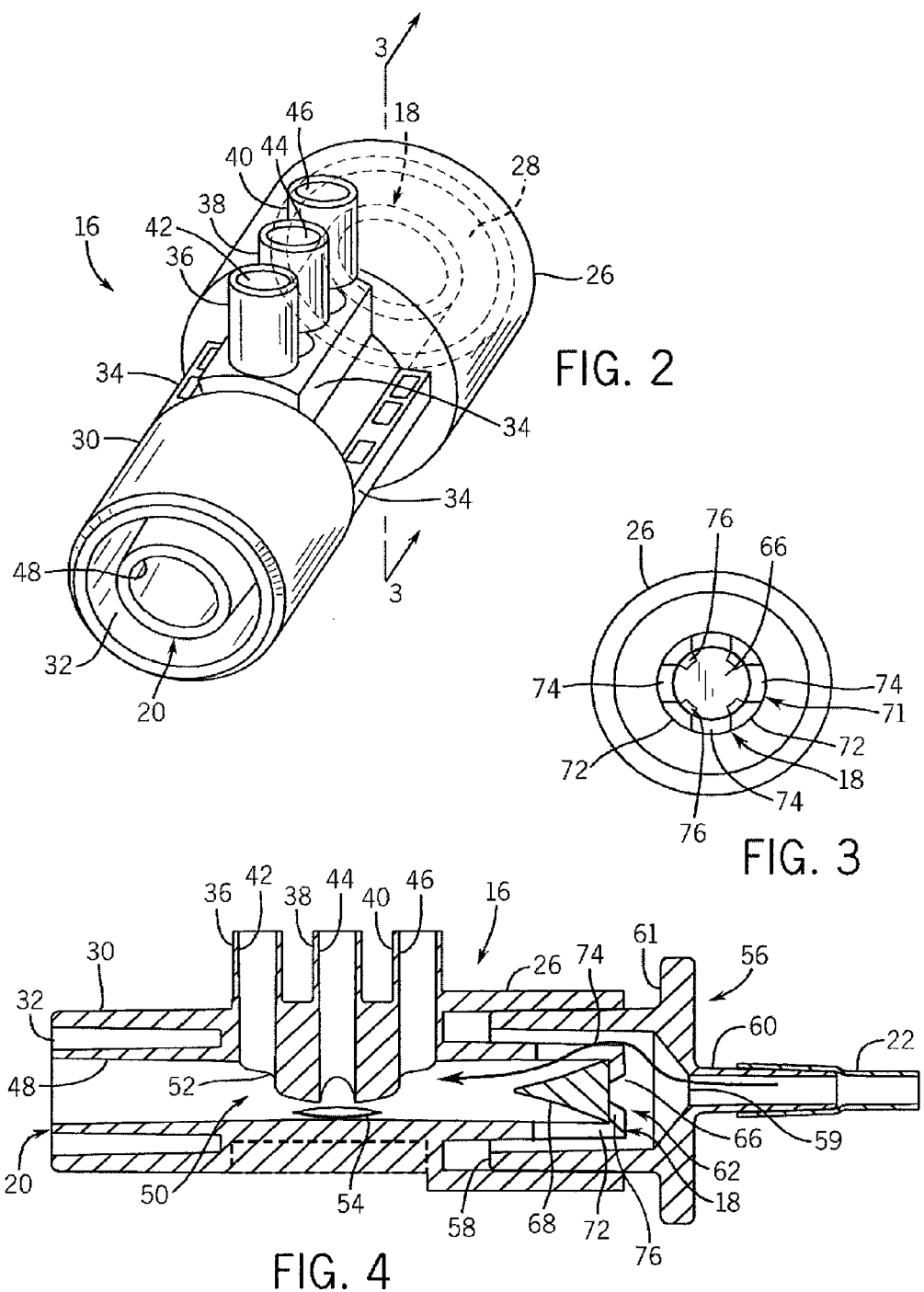

GAS FLOW DIVERTER FOR RESPIRATORY MONITORING DEVICE

CROSS-REFERENCE TO RELATED APPLICATIONS

This application is a divisional patent application U.S. application Ser. No. 10/863,697 and claims priority to U.S. Pat. No. 7,878,980 filed on Jun. 8, 2004 which claims priority to U.S. provisional application 60/478,706 filed on Jun. 13, 2003, the entirety of which are expressly incorporated herein.

FIELD OF THE INVENTION

The present invention relates to respiratory monitoring devices, and more specifically to a monitoring device with a gas flow diverter adapted specifically for use with infants.

BACKGROUND OF THE INVENTION

In order to measure the content of gas inhaled and exhaled by a patient utilizing a respirator, a monitoring device is often connected to the gas lines extending between the patient and the respirator in contact with the gases directed to and expired from the patient. To measure the volume and/or mass of the gas passing between the patient and the respirator, the monitoring device includes a sensor disposed within the path of the flowing gas in order to provide data on the gas flow that can be utilized to quantitatively determine the amount (volume and/or mass) of gas inhaled and/or exhaled by the patient.

For most sensors of this type, the gas flow is passed through a tube section of the sensor incorporating a type of restriction, and preferably a venturi, which creates a pressure drop between the inlet for the gas flow and the outlet for the gas flow from the tube section when the gas is flowing in either direction. This pressure difference is ascertained by a measuring device which senses the pressures at the gas flow inlet and gas flow outlet of the restriction in order to determine a corresponding flow rate for the gas flow which can then be used to determine the volumetric and/or mass flow rate of the gas.

However, based on the configuration of the restriction in the tube sections, in certain applications the measuring device is not capable of accurately determining the pressure differential within the tube section. More particularly, with regard to neonatal applications, due to the small volume of gas flowing into and out of the patient, with certain tube section designs the gas flow may pass completely through the center of the tube section without contacting the restriction. By not contacting the restriction, there is no consequent measurable pressure drop in the gas flow across the restriction. As a result, it is impossible for the measuring device to determine a volumetric and/or mass flow rate of the gas flowing through the tube section in order to effectively monitor the patient.

Therefore, it is desirable to develop a respirator sensor with a the tube section that is capable of directing the flow of gas through the tube section in a manner which ensures that the gas flow will contact the restriction present in the tube section, regardless of the size of the flow of gas. As a result, the tube section creates an effective pressure drop across the restriction within the section that can be measured by the measuring device to provide an accurate measurement of the volumetric or mass flow rate of the gas inhaled and exhaled by the patient. Further, it is desirable to form a device for this purpose that can be incorporated into original tube section constructions or can be used to retrofit existing tube sections in order to reduce the time and expense of forming tube sections with the device that is suitable for neonatal use.

SUMMARY OF THE INVENTION

According to a primary aspect of the present invention, a respirator sensor is provided that includes a generally hollow tubular section including a restriction, e.g., a venturi located within the center of the tube section. The tube section also includes a number of sampling sleeves or taps spaced along the restriction which withdraw a small amount of the gas flowing through the restriction at various points along the restriction in order to ascertain the magnitude of the pressure drop occurring across the restriction. The restriction disposed within the tube section does not extend completely across the interior of the tube section, such that gas is capable of flowing through the tube section around the restriction, thereby causing the measurable pressure drop.

In order to ensure that very small volume gas flows do not flow through the tube section without at least partially contacting the restriction to generate a measurable pressure drop, the tube section includes a baffle or gas flow diverter disposed within a gas flow inlet end of the sensor. The diverter is positioned on the tube section such that the entire gas flow contacts the diverter prior to entering the tube section. The shape of the diverter forces the gas flow to the outer portions of the passage through the tube section and subsequently allows a portion of the gas flow to flow into the center of the passage such that the gas flow is dispersed across the entire cross-sectional area of the tube section prior to encountering the restriction. Thus, the diverter serves to disperse the incoming flow of gas across the entire cross-sectional area of the interior of the tube section such that at least a portion of the incoming gas flow contacts the restriction to cause a measurable pressure drop in the gas flow as it flows across the restriction.

According to another aspect of the present invention, the gas flow diverter can be releasably attached to the tube section in the form of an adapter such that the tube section and sensor can be quickly and easily modified for use in either a conventional or a neonatal measurement and monitoring operation.

Numerous other aspects, features and advantages of the present invention will become apparent from the following detailed description taken together with the drawing figures.

BRIEF DESCRIPTION OF THE DRAWINGS

The drawings illustrate the best mode currently contemplated of practicing the present invention.

In the drawings:

FIG. 2 is an isometric view of the tube section of FIG. 1;

FIG. 3 a cross-sectional view along line 3-3 of FIG. 2;

FIG. 4 is a cross-sectional view of the tube section of FIG. 2 with a neonatal tube adapter attached;

DETAILED DESCRIPTION OF THE INVENTION

Figure 1:
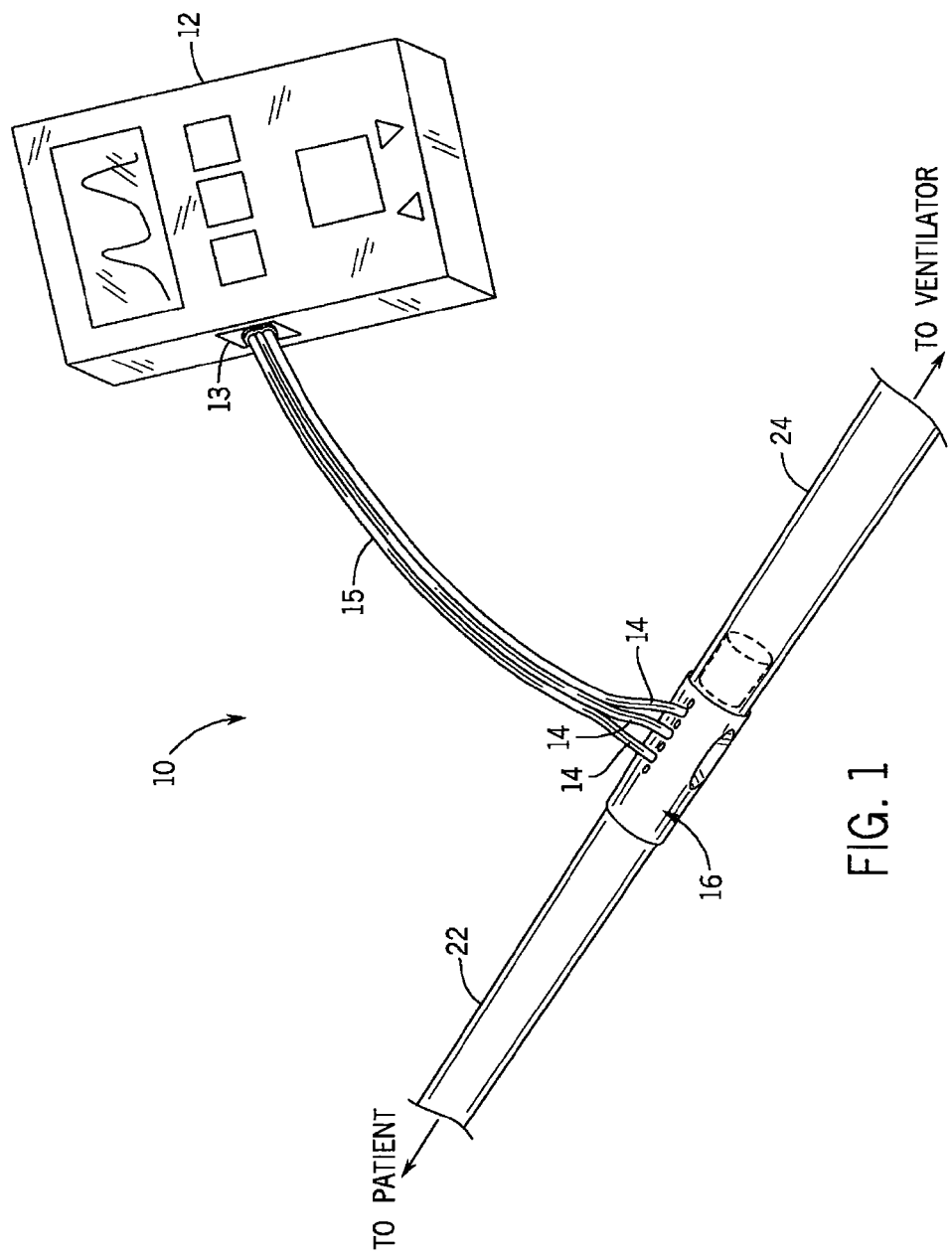
FIG. 1 is an isometric view of a respiratory sensor including a tube section connected between respiratory tubes and having a gas flow diverter constructed according to the present invention.

With reference now to the drawing figures in which like reference numerals designate like parts throughout the disclosure, a respiratory sensor is indicated generally at 10 in FIG. 1. The sensor 10 is formed of a control housing 12 including a removable plug 13 from which extends a number of measuring lumens 14 formed integrally with one another in a bundle 15. The lumens 14 are connected opposite the housing 12 to a tube section 16 having an inlet end 18 and an outlet end 20. The tube section 16 can be formed of any suitable rigid, non-porous material, and is preferably formed from a hard plastic which allows the tube section 16 to be formed using any compatible molding process. The respective ends 18 and 20 of the tube section 16 are each connected to tubes 22 and 24 which are in turn connected to a patient and a ventilator (not shown) in order to direct gases from and into both the patient and the ventilator through the tube section 16. The particular construction of the sensor 10 can vary from that shown in FIG. 1, with alternative constructions for the sensor 10 being disclosed in U.S. Pat. No. 5,929,831, commonly assigned with this application and incorporated herein by reference.

Referring now to FIGS. 2-4, the inlet end 18 has a collar 26 concentrically disposed around the inlet end 18 to form an inlet tube connection 28. The outlet end 20 also has a collar 30 concentrically disposed around the outlet end 20 to form an outlet tube connection 32. Between the collars 26 and 30, the tube section 16 includes a number of reinforcing ribs 34 that extend between the collars 26 and 30 to increase the rigidity and durability of the tube section 16. One of the ribs 34 further defines a number of taps or sampling sleeves 36, 38 and 40 to which the lumens 14 are each connected. Each of the sleeves 36-40 defines an aperture 42-46 therein that extends through the associated sleeve 36-40 and the aligned rib 34 into the interior of the tube section 16. The connection of each of the lumens 14 to the sleeves 36-40 allows portions of the gas flowing through the tube section 16 to be directed along the lumens 14 to the control housing 12 for use in calculating and monitoring the flow rate of the gas flowing through the tube section 16.

Between the inlet end 18 and outlet end 20, the tube section 16 defines an interior passage 48 through which the respiratory gases flow. The passage 48 includes a restriction, which is preferably in the shape of a venturi 50 disposed, approximately equidistant, between the inlet end 18 and the outlet end 20. The restriction 50 includes a main restricting member 52 that extends into the passage 48 in alignment with the rib 34 through which the apertures 42-46 extend, such that the apertures 42-46 also extend through the member 52 into fluid communication with the passage 48. The restriction 50 also preferably includes a pair of fins 54 disposed generally opposite the main restricting member 52 and are spaced from one another. In a particularly preferred embodiment, the size of the main restricting member 52 is significantly larger than the size of the fins 54, such that the main restricting member 52 extends into the passage 48 past the centerline of the passage 48, in order to most effectively turbulate the flow of gas through the passage 48 to cause a pressure drop in the gas flow across the restriction 50. In a preferred embodiment, the restricting member 52 and fins 54 have generally arcuate or curved outer surfaces located within the passage 48 such that the main member 52 and fins 54 operate to redirect the respiratory gas flow through the passage 48 into contact with each other, thereby creating a generally turbulent gas flow within the passage 48. This causes the consequent pressure reduction across the restriction 50 which can be measured by sampling the gas flow at each end of the restricting member 52 through the apertures 42-46. The pressure of the gas sampled at the apertures 42-46 and transmitted along the lumens 14 connected between sleeves 36-40 and the control housing 12 can then be utilized to determine the volume and/or mass flow rate of the gas flowing through the passage 48 and to monitor the breathing of the patient.

Due to variations in the configurations of the inlet end 18 and outlet end 20 of tube sections 16 made by different manufacturers, on certain occasions, e.g., when the sensor 10 is used in a neonatal application, the tube section 16 must be connected to an adapter 56 to properly attach and locate the tube 22 extending between the patient (not shown) and the tube section 16. The adapter 56 includes a sleeve 58 engageable with the inlet connection 28 between the inlet end 18 and the collar 26, and having a central opening 59 disposed in alignment with a nozzle 60 disposed opposite and extending outwardly from the sleeve 58. The nozzle 60 is connected to the tube 22 extending from the patient and directs the respiratory gases into and out of the adapter 56 and the tube section 16. The adapter 56 also includes gripping plate 61 integrally formed with and between the sleeve 58 and the nozzle 60 and through which the central opening 59 extends to facilitate the engagement of the adapter 56 with tube section 16.

In order to ensure that the incoming gas stream passing through the adapter 56 into the tube section 16 contacts the restricting member 52 in a manner which produces a turbulent gas flow and a consequent pressure drop across the restriction 50 when the gas flow is small, e.g., when the patient is an infant, in one embodiment of the invention the inlet end 18 of the tube section 16 includes a baffle or gas flow diverter 62 positioned therein. The diverter 62 is positioned concentrically with respect to the inlet end 18, passage 48, and the adapter nozzle 60, such that the incoming respiratory gas flow strikes the gas flow diverter 62 and is deflected around the diverter 62 substantially equally across the entire cross-sectional area of the passage 48.

Figure 5:
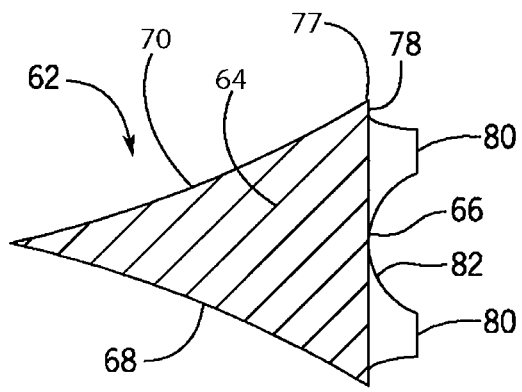
FIG. 5 is a side plan view of the gas flow diverter constructed according to the present invention.
Figure 6:
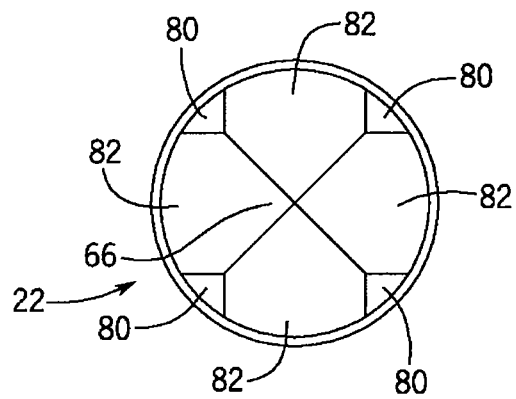
FIG. 6 is an end plan view of the gas flow diverter of FIG. 5.

As best shown in FIGS. 4-6, in a preferred embodiment, the gas flow diverter 62 is formed with a body 64 having a flat or otherwise generally blunt end 66 positioned adjacent the inlet end 18, and an inwardly tapering, frustoconical section 68 extending into the passage 48 from the flat end 66. The tapering section 68 can extend away from the flat end 66 in a strictly conical fashion, or may be formed to have a slightly concave surface 70, as best shown in FIG. 5, to assist in diverting the gas flow across the entire passage 48 within the tube section 16. The diverter 62 can be formed of any suitable non-porous material, which can be rigid or semi-rigid in order to facilitate the insertion of the diverter 62 into the tube section 16. However, in a preferred embodiment, the diverter 62 is formed of a metal, such as a stainless steel or aluminum, plastic or a rubber that is easily sterilizable for use with the tube section 16.

The diverter 62 can be secured within the passage 46 at the inlet end 18 using any suitable means 71; such as an adhesive or a mechanical fastener, so long as the incoming gas flow is permitted to pass around the diverter 62 and into the passage 48. In a preferred embodiment, the diverter 62 is secured within inlet end 18 by one or more locking members such as a number of deflectable fingers 72 formed on the inlet end 18 of the tube section 16 and engaged with the periphery of the flat end 66. The fingers 72 are separated by slots 74 through which the respiratory gas stream striking the flat end 66 can flow into the passage 48. The slots 74 disposed between the fingers 72 also enable each of the fingers 72 to be deflected slightly as the diverter 62 is inserted between the fingers 72. Each finger 72 slides along the frustoconical section 68 of the body 64 until a locking tab or tabs 76 located on the outermost end of the fingers 72 engage corresponding notches 78 disposed on the flat end 66 of the diverter 62. In a particularly preferred embodiment, the notches 78 are formed as a circumferential ridge disposed around the periphery 77 of flat end 66. In this position, the diverter 62 is held by the fingers 72 concentrically with regard to the passage 48 defined by the tube section 16 during use of the sensor 10.

Looking now at FIGS. 5 and 6, in a preferred embodiment, the flat end 66 is formed with a number of protrusions 80 thereon that extend outwardly from the flat end 66 in a direction opposite the frustoconical section 68. The protrusions 80 define a number of ports 82 there between which are spaced from one another around the flat end 66 by the protrusions 80. Any number of protrusions 80 and ports 82 can be formed on the flat end 66, such that the number and positioning of the protrusions 80 and ports 82 on the flat end 66 can be defined as desired in order to direct the incoming gas flow striking the flat end 66 through the ports 82 and into the passage 48 at the desired locations. In a particularly preferred embodiment, four spaced protrusions 80 are formed on the flat end 66 to form four ports 82 between the protrusions 80 spaced equidistant from one another and at right angles to one another. These ports 82 are positioned in alignment with the slots 74 such that the portion of the gas flow passing through each port 82 subsequently enters the tube section 16 through the aligned slot 74.

In operation, once the adapter 56 has been engaged with the inlet connection 28, the incoming gas flow through the tube 22 passes into the nozzle 60 of the adapter 56 and strikes the flat end 66 of the diverter 62. The incoming gas flow is directed by the protrusions 80 and ports 82 around the diverter 62 and through the slots 74 into the passage 48. The portions of the gas flow passing through each slot 74 is allowed to expand along the concave surface 70 of the diverter 62 to fill the entire cross-sectional area of the passage 48. Thus, at least a portion of the incoming gas flow is directed to impinge upon the main restricting number 52 while passing through the restriction 50 in order to generate a turbulent gas flow and a resulting pressure drop across the sampling sleeves 36-40.

EXPERIMENTAL

To illustrate the effectiveness of the diverter 62 in creating measurable pressure drops within the tube section 16 of a sensor 10 with small incoming gas flows, a number of different experiments run utilizing tube sections 16 of various configurations both including and omitting the gas flow diverter 62. In each of the experiments, a tube section 16 was connected to a 2.5 millimeter endotracheal tube through which a gas was pumped at flow rates varying from 5 ml/sec to 200 ml/sec. For each tube section 16 tested, the average inspired pressure and the maximum and minimum expired pressures were measured using the sampling sleeves 36-40. The error percent for the maximum pressure and minimum pressure were calculated from the average, maximum and minimum pressure values, and subtracted from one another to determine the total expiratory error which is illustrated in each of Tables 1-7 and in the graph illustrated in FIG. 7.

TABLE 1

Competitive Tube

| | | | | | | | | | | |
|---|---|---|---|---|---|---|---|---|---|---|
| Flow in liters/min. | 0.3 | 0.6 | 1.2 | 1.8 | 2.4 | 3 | 4.5 | 6 | 9 | 12 |
| VOLUME: ml | 10 | 20 | 40 | 60 | 80 | 100 | 150 | 200 | 300 | 400 |
| FLOW: ml/sec | 5 | 10 | 20 | 30 | 40 | 50 | 75 | 100 | 150 | 200 |
| avg inspired pressure | 0.275 | 0.877 | 1.63 | 2.473 | 3.27 | 4.02 | 6.05 | 8.25 | 12.25 | 16.15 |
| max expired pressure | 0.334 | 0.897 | 2.06 | 3.88 | 5.13 | 4.92 | 6.37 | 8.49 | 12.84 | 17.02 |
| min expired pressure | 0.309 | 0.786 | 1.41 | 2.17 | 2.72 | 3.91 | 6.24 | 8.412 | 12.64 | 15.96 |
| max expired % error | 21 | 2 | 26 | 57 | 57 | 22 | 5 | 3 | 5 | 5 |
| min expired % error | 12 | −10 | −13 | −12 | −17 | −3 | 3 | 2 | 3 | −1 |
| Total expired error | 9 | 13 | 40 | 69 | 74 | 25 | 2 | 1 | 2 | 7 |

TABLE 2

CPT - Old Tube Design

| | | | | | | | | | | |
|---|---|---|---|---|---|---|---|---|---|---|
| Flow in liters/min. | 0.3 | 0.6 | 1.2 | 1.8 | 2.4 | 3 | 4.5 | 6 | 9 | 12 |
| VOLUME: ml | 10 | 20 | 40 | 60 | 80 | 100 | 150 | 200 | 300 | 400 |
| FLOW: ml/sec | 5 | 10 | 20 | 30 | 40 | 50 | 75 | 100 | 150 | 200 |
| avg inspired pressure | 0.238 | n/r | 1.247 | n/r | n/r | 1.967 | 4.58 | 6.16 | 9.23 | 12.08 |
| max expired pressure | 0.16 | n/r | n/r | n/r | n/r | n/r | 4.58 | 6.19 | 9.39 | 11.96 |
| min expired pressure | 0.15 | n/r | n/r | n/r | n/r | n/r | 4.55 | 6.14 | 9.26 | 12.13 |
| max expired % error | −33 | n/r | −100 | n/r | n/r | −100 | 0 | 0 | 2 | −1 |
| min expired % error | −37 | n/r | −100 | n/r | n/r | −100 | −1 | 0 | 0 | 0 |
| CPT old total expired error | 4 | n/r | 0 | n/r | n/r | 0 | 1 | 1 | 1 | −1 |

*n/r—no reading

TABLE 3

CPT New Tube Design Without Baffle

| Flow in liters/min. | 0.3 | 0.6 | 1.2 | 1.8 | 2.4 | 3 | 4.5 | 6 | 9 | 12 |
|---|---|---|---|---|---|---|---|---|---|---|
| VOLUME: ml | 10 | 20 | 40 | 60 | 80 | 100 | 150 | 200 | 300 | 400 |
| FLOW: ml/sec | 5 | 10 | 20 | 30 | 40 | 50 | 75 | 100 | 150 | 200 |
| avg inspired pressure | 0.429 | 0.86 | 1.73 | 2.63 | 3.62 | 4.609 | 7.018 | 9.158 | 12.94 | 16.54 |
| max expired pressure | 0.3 | 0.8 | n/r | n/r | n/r | n/r | 6.78 | 9.95 | 12.88 | 16.55 |
| min expired pressure | 0.25 | 0.39 | n/r | n/r | n/r | 0.445 | 6.5 | 9.87 | 12.59 | 16.01 |
| max expired % error | −30 | −7 | −100 | −100 | −100 | −100 | −3 | 9 | 0 | 0 |
| min expired % error | −42 | −55 | −100 | −100 | −100 | −90 | −7 | 8 | −3 | −3 |
| CPT new no invention | 12 | 48 | 0 | 0 | 0 | −10 | 4 | 1 | 2 | 3 |

*n/r—no reading

TABLE 4

CPT - Old Tube Design With Sieve

| Flow in liters/min. | 0.3 | 0.6 | 1.2 | 1.8 | 2.4 | 3 | 4.5 | 6 | 9 | 12 |
|---|---|---|---|---|---|---|---|---|---|---|
| VOLUME: ml | 10 | 20 | 40 | 60 | 80 | 100 | 150 | 200 | 300 | 400 |
| FLOW: ml/sec | 5 | 10 | 20 | 30 | 40 | 50 | 75 | 100 | 150 | 200 |
| avg inspired pressure | 0.187 | 0.593 | 1.208 | 1.78 | 2.37 | 2.92 | 4.45 | 5.98 | 8.935 | 11.73 |
| max expired pressure | 0.19 | 0.58 | 1.1 | 1.55 | 2.25 | 2.9 | 4.44 | 5.99 | 9.04 | 11.92 |
| min expired pressure | 0.165 | 0.535 | 0.96 | 1.16 | 1.63 | 2.23 | 4.41 | 5.95 | 8.97 | 11.85 |
| max expired % error | 2 | −2 | −9 | −13 | −5 | −1 | 0 | 0 | 1 | 2 |
| min expired % error | −12 | −10 | −21 | −35 | −31 | −24 | −1 | −1 | 0 | 1 |
| CPT old with sieve | 13 | 8 | 12 | 22 | 26 | 23 | 1 | 1 | 1 | 1 |

TABLE 5

CPT - New Tube Design With Sieve

| Flow in liters/min. | 0.3 | 0.6 | 1.2 | 1.8 | 2.4 | 3 | 4.5 | 6 | 9 | 12 |
|---|---|---|---|---|---|---|---|---|---|---|
| VOLUME: ml | 10 | 20 | 40 | 60 | 80 | 100 | 150 | 200 | 300 | 400 |
| FLOW: ml/sec | 5 | 10 | 20 | 30 | 40 | 50 | 75 | 100 | 150 | 200 |
| avg inspired pressure | 0.210 | 0.540 | 1.200 | 1.770 | 2.380 | 3.000 | 4.580 | 6.200 | 9.270 | 12.050 |
| max expired pressure | 0.165 | 0.410 | 1.090 | 1.600 | 2.020 | 2.910 | 4.510 | 6.120 | 9.350 | 12.300 |
| min expired pressure | 0.145 | 0.380 | 0.860 | 1.100 | 1.380 | 1.990 | 4.430 | 6.040 | 9.040 | 11.900 |
| max expired % error | −21 | −24 | −9 | −10 | −15 | −3 | −2 | −1 | 1 | 2 |
| min expired % error | −31 | −30 | −28 | −38 | −42 | −34 | −3 | −3 | −2 | −1 |
| CPT new with sieve | 10 | 6 | 19 | 28 | 27 | 31 | 2 | 1 | 3 | 3 |

TABLE 6

CPT - New Tube Design With Baffle With Four Slots

| Flow in liters/min. | 0.3 | 0.6 | 1.2 | 1.8 | 2.4 | 3 | 4.5 | 6 | 9 | 12 |
|---|---|---|---|---|---|---|---|---|---|---|
| VOLUME: ml | 10 | 20 | 40 | 60 | 80 | 100 | 150 | 200 | 300 | 400 |
| FLOW: ml/sec | 5 | 10 | 20 | 30 | 40 | 50 | 75 | 100 | 150 | 200 |
| avg inspired pressure | 0.221 | 0.6 | 1.24 | 1.89 | 2.56 | 3.13 | 4.81 | 6.53 | 9.73 | 12.56 |
| max expired pressure | 0.219 | 0.61 | 1.22 | 1.88 | 2.57 | 3.19 | 4.88 | 6.58 | 9.99 | 13.05 |
| min expired pressure | 0.196 | 0.62 | 1.21 | 1.81 | 2.49 | 3.11 | 4.84 | 6.52 | 9.96 | 12.99 |
| max expired % error | −1 | 2 | −2 | −1 | 0 | 3 | 1 | 1 | 3 | 4 |
| min expired % error | −11 | 3 | −2 | 2 | −3 | −1 | 1 | 0 | 2 | 3 |
| CPT new with invention | 10 | −2 | 1 | −2 | 3 | 4 | 1 | 1 | 0 | 0 |

Figure 7:
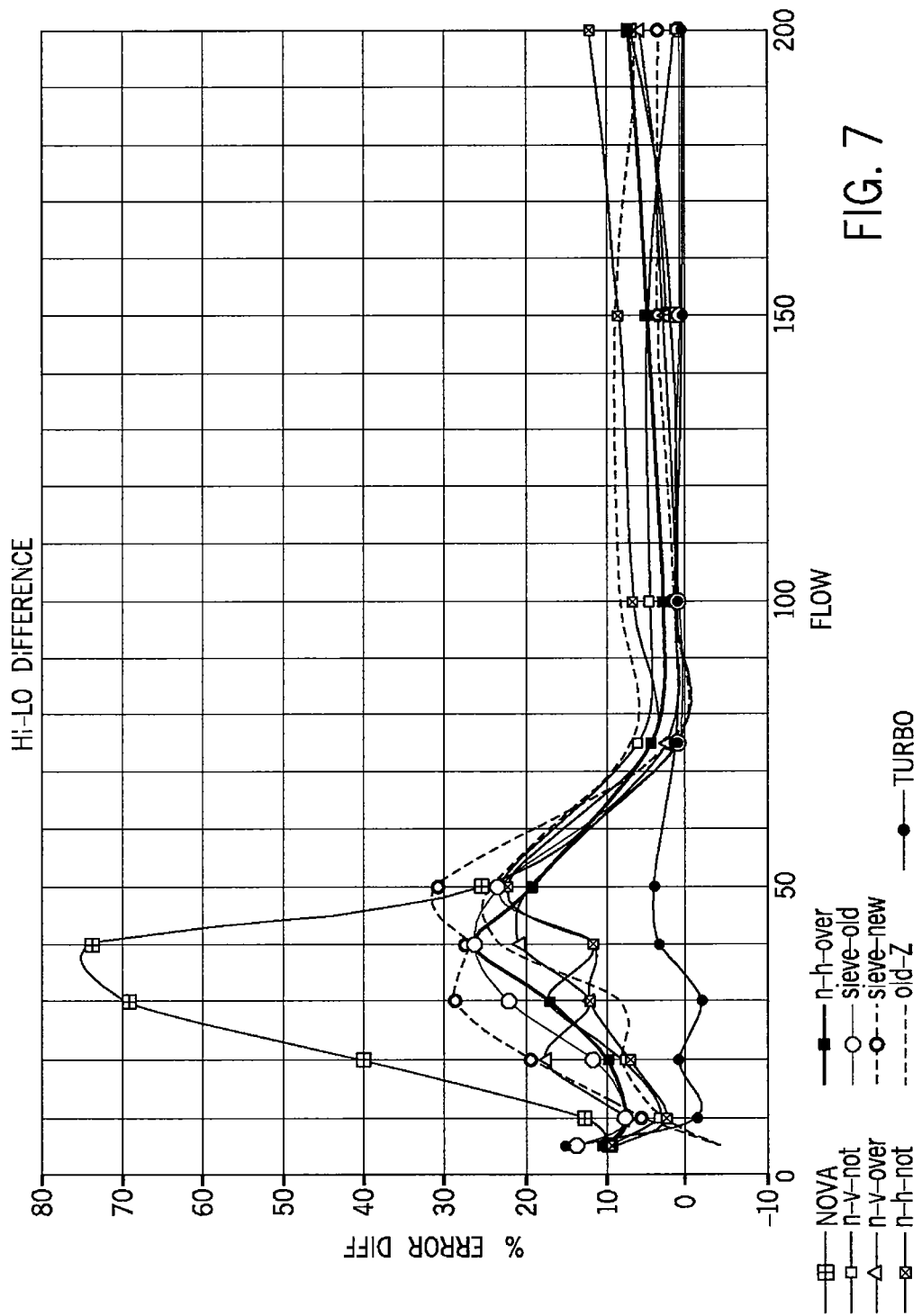
FIG. 7 is a graph illustrating the error in gas flow measurements generated by various tube section designs at low gas flow volumes in comparison with the measurement errors created by the tube section and diverter of the present invention.

As seen in the results in each of Tables 1-6 and in the graph and FIG. 7, while the total expired error percent at very low volumetric flow rates was out of specification for each of the tube sections 16 utilized without the gas flow diverter 62, the tube section 16 including the diverter 62 tested obtained accurate gas flow pressure readings for volumetric flow rates down to approximately 5 ml/sec. As a result, these results show that the diverter 62 is highly effective at causing a very small incoming gas flow to impinge upon the restrictions present in a tube section 16 of a sensor 10 in order to obtain accurate pressure differential measurements within the tube section 16 for monitoring the breathing of the patient.

Further, in separate testing done with diverters 62 having different port 82 configurations, the effect of blocking various ports 82 had a negligible effect on ability of the diverter 62 to effectively turbulate the gas stream. As represented in Table 7, data was collected on the valve of the inspired portion (positive plateau) and the highest and lowest values for the expired portion (negative plateau) of the breath or gas flow flowing through the tube section 16 with a diverter 62 having various ports 82 blocked. This data was then utilized to determine a percent difference between the maximum and minimum negative plateau values. As seen in the results illustrated in Table 7, all of the valves for the percent difference came out within the range for normal measurement errors. Thus, the blocking of any combination of ports 82 does not have any affect on the effectiveness of the diverter 62 to turbulate on expired gas flow.

TABLE 7

| Ports blocked | Positive Plateau 10 | Negative Plateau Highest | Negative Plateau Lowest | Hi-lo diff. | % diff | Port #1 | Port #2 | Port #3 | Port #4 |
|---|---|---|---|---|---|---|---|---|---|
| 1 | 2.49 | 2.56 | 2.53 | 0.03 | 1.2 | 1.2 | | | |
| 2 | 2.48 | 2.57 | 2.45 | 0.12 | 4.8 | | 4.8 | | |
| 3 | 2.5 | 2.52 | 2.46 | 0.06 | 2.4 | | | 2.4 | |
| 3, 1 | 2.5 | 2.56 | 2.44 | 0.12 | 4.8 | 4.8 | | 4.8 | |
| 3, 2 | 2.5 | 2.49 | 2.46 | 0.03 | 1.2 | | 1.2 | 1.2 | 2.8 |
| 4, 2 | 2.48 | 2.52 | 2.45 | 0.07 | 2.8 | | 2.8 | | 1.6 |
| 4, 2, 1 | 2.5 | 2.53 | 2.49 | 0.04 | 1.6 | 1.6 | 1.6 | 4 | |
| 1, 2, 3 | 2.5 | 2.57 | 2.47 | 0.1 | 4 | 4 | 4 | 2.4 | 2.4 |
| 4, 2, 3 | 2.49 | 2.46 | 2.4 | 0.06 | 2.4 | | 2.4 | | |
| none | 2.48 | 2.52 | 2.45 | 0.07 | 2.7 | | | | |

Figure 8:
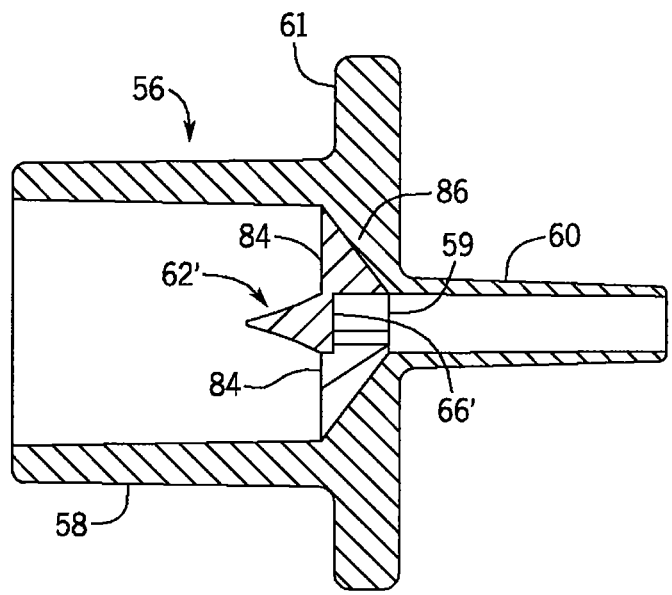
FIG. 8 is a cross-sectional view of a second embodiment of the present invention.
Figure 9:
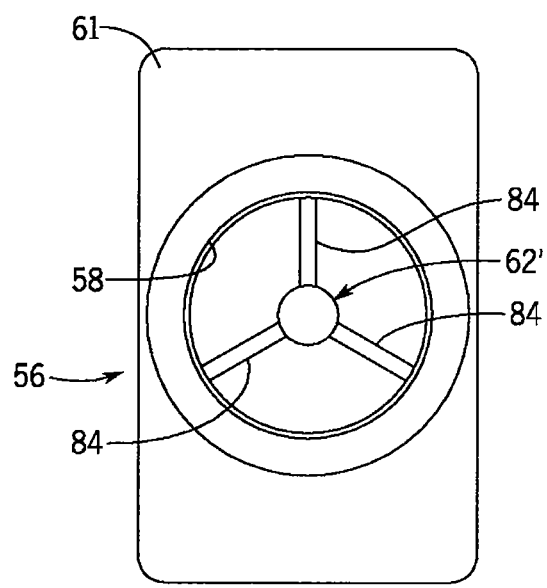
FIG. 9 is an end plan view of the second embodiment of FIG. 8.

While it is preferred to position the diverter 62 within the passage 48 formed by the tube section 16, it is also contemplated that the diverter 62 can be located on other suitable sections of the sensor 10 to provide the identical function. For example, as best shown in FIGS. 8 and 9, in a second embodiment the adapter 56 is illustrated in which a number of ribs 84 are formed within a tapering section 86 of the sleeve 58 positioned adjacent nozzle 60. The ribs 84 surround the central opening 59 within which can be secured to a diverter 62' in a position concentric to the nozzle 60 and passage 48. The diverter 62' is formed virtually identically to the diverter 62 discussed previously. However, the diverter 62' is formed to have an overall diameter at the flat end 66' that is similar to the diameter of the nozzle 60 and not the diameter of the passage 48. The diverter 62' can be press-fit between the ribs 84 and/or secured there between by any suitable securing means, such as an adhesive or a mechanical fastener. Alternatively, the diverter 62' and ribs 84 can be molded to the adapter 56 as a single unit. In this embodiment, an incoming gas flow through the tube 22 passes into the nozzle 60 and is directed from the nozzle 60 directly against the flat end 66' of the diverter 62'. Upon striking the flat end 66', the gas flow passes around the diverter 62' and between the ribs 84 into the inlet end 18 of the tube section 16 in the manner described with regard to the diverter 62. The incoming gas flow is thus turbulated by the diverter 62' and is caused to flow in turbulent fashion into the tube section 16 and restriction 50 to provide accurate readings regarding the pressure drop across the restriction 50.

Various alternatives are contemplated as being within the scope of the following claims particularly pointing out and distinctly claiming the subject matter regarded as the invention.

I hereby claim:

1. A tube section for a respiratory measurement device, the tube section comprising:
   a) a tubular member defining an interior passage, an inlet end and an outlet end;
   b) at least one restricting member disposed within the tubular member to create a pressure drop in a gas flow flowing through the tubular member;
   c) a number of measuring sleeves spaced from one another and extending through the tubular member and the at least one restriction into the interior passage; and
   d) a gas flow diverter positioned concentrically with the inlet end of the tubular member and offset longitudinally toward the inlet from the at least one restricting member and the number of measuring sleeves, the diverter including a blunt surface disposed adjacent the inlet end and a generally tapered surface extending from the blunt surface towards the interior passage and ending short of the at least one restricting member.

2. The tube section of claim 1 wherein the inlet end is formed with at least one locking member adapted to hold the diverter in engagement with the tubular member.

3. The tube section of claim 2 wherein the at least one locking member is deflectable along the generally tapered surface of the gas flow diverter and engages a periphery of the diverter.

4. The tube section of claim 2 wherein the inlet end includes a number of locking members separated by slots.

5. The tube section of claim 4 wherein the diverter includes a number of ports disposed in alignment with the slots defined between the number of locking members.

6. The tube section of claim 1 further comprising an adapter positionable over the inlet end, the adapter including a housing engageable with the inlet end, and a nozzle in fluid communication with and extending outwardly from the housing, wherein the diverter is secured to the adapter within the housing.

7. The tube section of claim 6 wherein the housing includes at least one rib located adjacent the nozzle and engageable with the diverter.

8. The tube section of claim 1 wherein the diverter includes a generally conical body with a concave surface.

9. A tube section for a respiratory measurement sensor, the tube section formed by the process of:
   a) providing a tubular member having an inlet end, an outlet end and defining an interior passage within which is disposed at least one restriction member, the at least one restriction member including a number of sampling sleeves spaced from one another and extending through the tubular member and the at least one restriction member to the interior passage; and
   b) engaging a gas flow diverter with the inlet end of the tubular member so that the gas flow diverter does not overlap a cross-section of the at least one restriction, the diverter including a generally blunt surface and a tapered surface extending from the blunt surface inwardly towards the interior passage.

10. The tube section of claim 9 wherein the step of engaging the diverter with the inlet end comprises interlocking a peripheral ridge disposed on the blunt surface end of the diverter with at least one locking member located on the inlet end.

11. The tube section of claim 9 wherein the step of engaging the diverter with the inlet end comprises:
 a) providing an adapter including a housing engageable with the inlet end and a nozzle in fluid communication with and extending outwardly from the housing, wherein the diverter is secured to the adapter within the housing; and
 b) interlocking the adapter with the inlet end.

* * * * *